United States Patent
Seibert et al.

(10) Patent No.: US 6,277,589 B1
(45) Date of Patent: Aug. 21, 2001

(54) METHOD AND APPARATUS FOR RAPID BIOHYDROGEN PHENOTYPIC SCREENING OF MICROORGANISMS USING A CHEMOCHROMIC SENSOR

(75) Inventors: Michael Seibert, Lakewood; David K. Benson; Timothy Michael Flynn, both of Golden, all of CO (US)

(73) Assignee: Midwest Research Institute, Kansas City, MO (US)

( * ) Notice: Subject to any disclaimer, the term of this patent is extended or adjusted under 35 U.S.C. 154(b) by 0 days.

(21) Appl. No.: 09/316,172

(22) Filed: May 21, 1999

Related U.S. Application Data

(60) Provisional application No. 60/086,313, filed on May 12, 1998.

(51) Int. Cl.$^7$ .................................................. C12Q 1/24
(52) U.S. Cl. ...................... 435/30; 204/424; 205/777.5
(58) Field of Search ........................... 435/30, 34, 287.5, 435/817; 204/424; 205/777.5; 427/126.3

(56) References Cited

U.S. PATENT DOCUMENTS

| | | |
|---|---|---|
| 3,567,383 | 3/1971 | Langley et al. . |
| 4,030,979 * | 6/1977 | Zuber ........................... 195/103.5 M |
| 4,324,760 | 4/1982 | Harris . |
| 4,324,761 | 4/1982 | Harris . |
| 4,442,211 * | 4/1984 | Greenbaum ........................ 435/168 |
| 4,661,320 * | 4/1987 | Ito et al. ................................ 422/86 |
| 5,367,283 | 11/1994 | Lauf et al. . |
| 5,668,301 | 9/1997 | Hunter . |
| 5,756,207 * | 5/1998 | Clough et al. ........................ 428/375 |
| 5,811,662 * | 9/1998 | Williams et al. .................... 73/31.06 |

FOREIGN PATENT DOCUMENTS

| | | |
|---|---|---|
| 42 20 932 * | 1/1994 | (DE) . |
| 5-3540 * | 5/1993 | (JP) . |
| 5-3892 * | 5/1993 | (JP) . |

OTHER PUBLICATIONS

Zaborsky, O. BioHydrogen. Plenum Press, NY, pp. 227–234, 1998.*

Ghirardi M. L. Generation of C. reinhardtii Mutants That Photoproduce H2 From H20 in the Presence of 02. Photosynthesis: Mechanisms and Effects vol. 3, pp. 1959–1962, 1998.*

* cited by examiner

*Primary Examiner*—Ralph Gitomer
(74) *Attorney, Agent, or Firm*—Paul J. White

(57) ABSTRACT

The invention provides an assay system for identifying a hydrogen-gas-producing organism, including a sensor film having a first layer comprising a transition metal oxide or oxysalt and a second layer comprising hydrogen-dissociative catalyst metal, the first and second layers having an inner and an outer surface wherein the inner surface of the second layer is deposited on the outer surface of the first layer, and a substrate disposed proximally to the outer surface of the second layer, the organism being isolated on the substrate.

11 Claims, 3 Drawing Sheets

METHOD AND APPARATUS FOR RAPID BIOHYDROGEN PHENOTYPIC SCREENING OF MICROORGANISMS USING A CHEMOCHROMIC SENSOR

CROSS REFERENCE TO RELATED APPLICATIONS

This 35 U.S.C. 111(a) application is filed pursuant to 35 U.S.C. 119(e)(1) for an invention disclosed in U.S. Provisional Application No. 60/086,313 entitled: A CHEMOCHROMIC SENSOR FOR RAPID BIOHYDROGEN PHENOTYPIC SCREENING, filed May 21, 1998.

CONTRACTUAL ORIGIN OF THE INVENTION

The United States Government has rights in this invention pursuant to Contract No.DE-AC36-98GO10337 between the United States Department of Energy and the Midwest Research Institute.

BACKGROUND OF THE INVENTION

1. Field of the Invention

This invention relates to chemochromic sensor films for use in rapidly screening isolate organisms capable of producing hydrogen.

2. Description of the Prior Art

Light-induced biological hydrogen production represents a potentially cost-effective system for the production of renewable non-polluting energy. Photobiological hydrogen production is catalyzed by nitrogenase and hydrogenase enzyme systems that are present in bacteria, photosynthetic bacteria, cyanobacteria, and green algae. Green algae, such as *Chlamydomonas reinhardtii*, can photoevolve hydrogen only through an inducible, reversible hydrogenase enzyme using water as the electron source. While hydrogenase-catalyzed hydrogen photo-production has potential as an efficient energy source, one of the major obstacles which currently limits any commercial application of this process is the deactivation of the hydrogenase enzyme in the presence of oxygen, produced in the water-splitting process of photosynthesis. Thus, it is desirable to isolate and select for bacterial, or algal mutant organisms which exhibit an oxygen-tolerant hydrogen production phenotypic response, in order to further the commercial production of light-induced hydrogen.

Two recent methods have been used in order to select for *C. reinhardtii* mutants which exhibit the oxygen tolerant hydrogen production phenotypic response. These methods are based on either the hydrogen production or hydrogen uptake activity of the reversible hydrogenase enzyme. The first approach is dependent on the ability of algal cells to produce hydrogen in competition with a drug that, when reduced, releases products toxic to the cells. Hydrogen production selective pressure is applied in the presence of increasing oxygen-stress to enrich for oxygen-tolerant organisms. The second approach is based on algal cell growth, using hydrogen as an electron source for carbon dioxide fixation. The addition of oxygen during the hydrogen uptake selection is then used to select for oxygen-tolerant organisms.

The evolution of hydrogen by an organism has been assayed amperometriclly. The amperometric determination uses a Clark type electrode that can be biased versus Ag/AgCl to determine either the hydrogen or oxygen concentration present in an assay chamber. Algal cells are induced under anaerobic conditions prior to the measurements. The algae are then anaerobically injected into an assay chamber containing an assay buffer (50 mM MOPS, pH 6.8), which is pre-adjusted to different initial concentrations of oxygen. The cells are then incubated in the dark and illuminated with a saturating heat-filtered incandescent light to induce hydrogen evolution. Initial hydrogen evolution rates are derived from the initial slopes of each curve, and gas concentrations are corrected for the decrease in aqueous solution solubility. A gas chromatograph can also be used to assay for hydrogen production capacity. However, these assays for oxygen-tolerant hydrogen photo-production are very costly, time consuming, and have been the prime rate limiting factor in the rapid identification and selection of more desirable mutant organisms.

Hunter, in U.S. Pat. No. 5,668,301 discloses a hydrogen sensitive metal alloy that contains palladium and titanium to provide a larger change in electrical resistance when exposed to the presence of hydrogen. The alloy is deposited on a substrate and a thin film is connected across electrical circuitry to provide a sensor device that can be used for improved sensitivity and accuracy of hydrogen detection.

U.S. Pat. No. 5,367,283 issued to Lauf et al., discloses a thin-film hydrogen sensor element comprised of an essentially inert, electrically-insulating substrate having a thin-film metallization deposited thereon which forms at least two resistors on the substrate. The metallization comprises a layer of Pd or a Pd alloy for sensing hydrogen and an underlying intermediate metal layer for providing enhanced adhesion of the metallization to the substrate. The difference in electrical resistances of the covered resistor and uncovered resistor is related to the hydrogen concentration in a gas to which the sensor element is exposed.

U.S. Pat. No. 4,324,761, issued to Harris, discloses a hydrogen detector comprised of a substrate supporting a electrically conducting base metal film, and upper electrically conducting diffusion barrier metal film, a polycrystalline film of titanium dioxide sandwiched between the base and diffusion barrier films, the polycrystalline titanium dioxide film electrically insulates the base film from the diffusion barrier film, the base film, being in electrical contact with the titanium dioxide film, an insulating layer electrically insulating the titanium dioxide film from the diffusion barrier film except for a predetermined surface portion thereof in electrical contact with the diffusion barrier film; wherein the predetermined electrically contacting portion is sufficiently large to produce a measurable electrical conductance, an electrically conducting or non-conducting catalytic top film of metal able to dissociate hydrogen into its atomic form in electrical contact with the diffusion barrier film and a least coextensive with the barrier film throughout the predetermined electrically contacting portion, as can best be seen in the cross-sectional view of FIG. 2.

U.S. Pat. No. 4,324,760 to Harris, disclosed a hydrogen detector having a substrate supporting an electrically conducting base metal film, an electrically conducting top film of metal able to dissociate hydrogen into atomic form, a polycrystalline film of titanium dioxide sandwiched between the base and top films, wherein the polycrystalline titanium dioxide film electrically insulates the base film from the top film, the base film being in electrical contact with the titanium dioxide film, an insulating layer electrically insulating the titanium dioxide film from the top film except for a predetermined surface portion thereof in electrical contact with the top film, and wherein the predetermined electrically contacting portion is sufficiently large to produce a measurable electrical conductance that varies with the concentration of hydrogen in the atmosphere surrounding it.

Each of the foregoing patents issued to Hunter, Lauf, et al., and Harris disclose electrical devices, which generate an electrical signal, determinative of the presence of hydrogen. However, these devices do not spatially resolve the point where the gas in produced in relation to the sample surface. Therefore, these devices would not be useful to discriminate the specific location of a colony which produces hydrogen gas where the sample, to be screened, consists of many colonies of the organism.

U.S. Pat. No. 3,567,383 issued to Langley et al. discloses a detector for hydrogen having as its sensing device a thin film comprised of palladium or platinum oxide, which oxide on contact with hydrogen reduces to the corresponding metal. The differences in properties, electrical or optical, of the oxide and metal film are used to detect the presence of hydrogen. While this patent provides an optical means for detecting hydrogen which could provide spatial resolution it does not provide the sensitivity (0.02% hydrogen concentration), rapid response rate (a few seconds), and economy in manufacture which are desirable for rapidly screening colonies of hydrogen-producing organisms on a substrate.

The development of a rapid screening method and device for the detection of hydrogen-producing mutants would greatly enhance the analysis of the survivors of selective pressure methods, in the rapid isolation of desirable mutant organisms. Furthermore, a rapid screening would assist in the analysis of mutants derived through a molecular biological approach to further the oxygen-tolerance of the hydrogenase enzyme.

Therefore, what is needed, is a rapid screening method for the oxygen-tolerant, light-induced hydrogen phenotype in mutant organisms.

SUMMARY

It is therefore an object of the present invention to rapidly screen for isolate microorganisms which exhibit an oxygen-tolerant hydrogen phenotype.

It is another object of the present invention to use a chemochromic film to detect isolate mutant colonies of green algae, which produce hydrogen under either anaerobic or aerobic conditions.

It is yet another object of the present invention to develop a screening assay for isolating individual oxygen-tolerant, hydrogen-producing, mutant green algae colonies having an assay sensitivity limit of at least a 4 nmoles of hydrogen evolved per colony of microorganism, to be screened.

Briefly, the invention provides a system for identifying a hydrogen-gas-producing organism, comprising a sensor film having a first layer comprising a transition metal oxide or oxysalt and a second layer comprising a hydrogen-dissociative catalyst metal, the first and second layers having an inner and an outer surface wherein the inner surface of the second layer is deposited on the outer surface of the first layer, and a substrate adjacent to the outer surface of the second layer, the organism located on the substrate.

Unless specifically defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

DESCRIPTION OF THE PREFERRED EMBODIMENTS

The present invention is a very sensitive chemochromic sensor film, and method for using the film, to detect the production of a gas in the presence of an isolate colony of a microorganism. The device comprises a chemochromic film placed in a spaced relationship to an isolate colony of a microorganism. The film exhibits a reversible color change, at a point just over the gas-producing colony, which varies in intensity depending on the concentration of gas produced. The color change occurs under either anaerobic or aerobic conditions.

In a preferred embodiment, the gas to be detected is hydrogen. The chemochromic film uses a layer system, having transition metal oxides or oxysalt 7 and a hydrogen dissociative catalyst metal 6, wherein the transition metal oxide or oxysalt 7 is selected from the group consisting of $WO_3$, $Nb_2O_3$ and $CoMoO_4$, and the hydrogen dissociative catalyst metal is selected from the group consisting of platinum, rhodium and palladium. The layer can further comprise a fluorinated hydrocarbon polymer 8 wherein the fluorinated hydrocarbon polymer comprises TEFLON. The chemochromic film is normally transparent. In a sensitization reaction, when hydrogen gas reacts with the tungsten trioxide, it causes a reversible blue color change which grows in intensity as the concentration of hydrogen increases. The hydrogen dissociative catalyst metal serves to accelerate this reaction. When hydrogen gas is removed from the vicinity of the film, hydrogen in the film diffuses to the film surface and escapes as hydrogen gas or is oxidized to water if oxygen is present, and the film returns to it's transparent state for reuse.

In another preferred embodiment a grid system, and a piece of filter paper are located over several colonies, growing on agar in a Petri dish, for phenotypic screening. When small quantities of hydrogen are produced in the vicinity of the film, the grid location of the sensor film blue coloration indicates the location of the colony which exhibits the oxygen-tolerant hydrogen phenotype. In this way, the sensor helps to identify which, among many colonies of microorganism is producing hydrogen gas under the selected experimental conditions.

Figure 1:
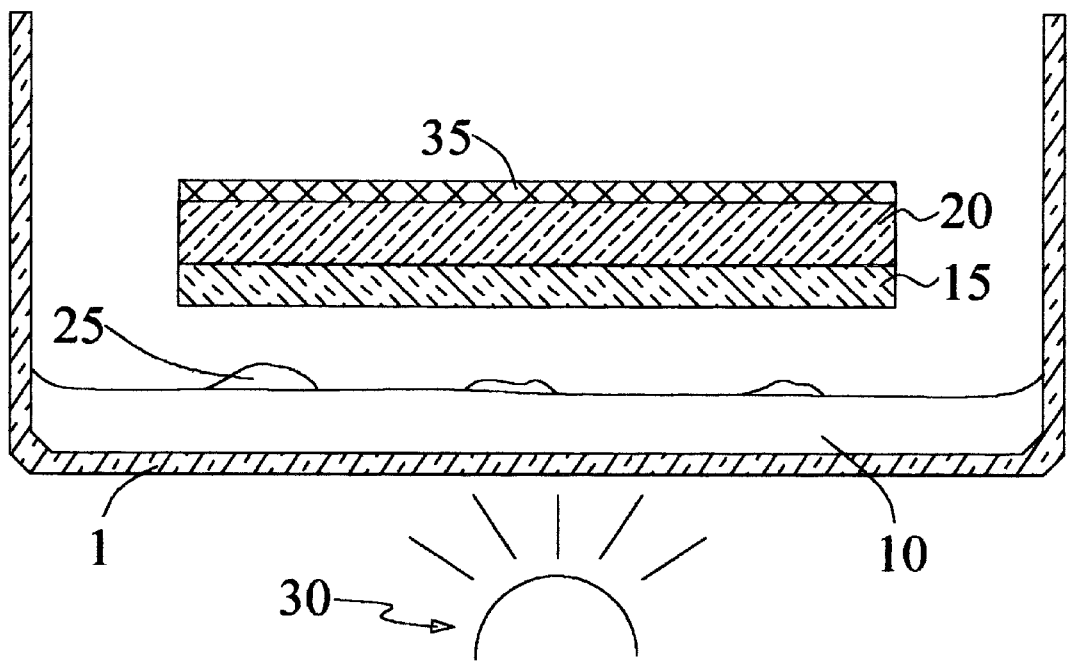
FIG. 1 is a side view of the preferred embodiment of the screening assay.

Referring now to the drawing figures, in which like numerals represent like features there is shown in FIG. 1 film 20 is a chemochromic film layer, positioned in plastic dish 1, on top of filter paper 15. On filter paper 15, grid 35 is positioned to locate isolate microorganism colony 25, which is growing on agar surface 10, poured into a transparent culture dish 1. Film 20 exhibits a color change at a point just over a hydrogen-producing colony 25. Film 20 exhibits the color change in the presence of hydrogen either under anaerobic or aerobic conditions, upon sensitization with light source 30.

Figure 2:
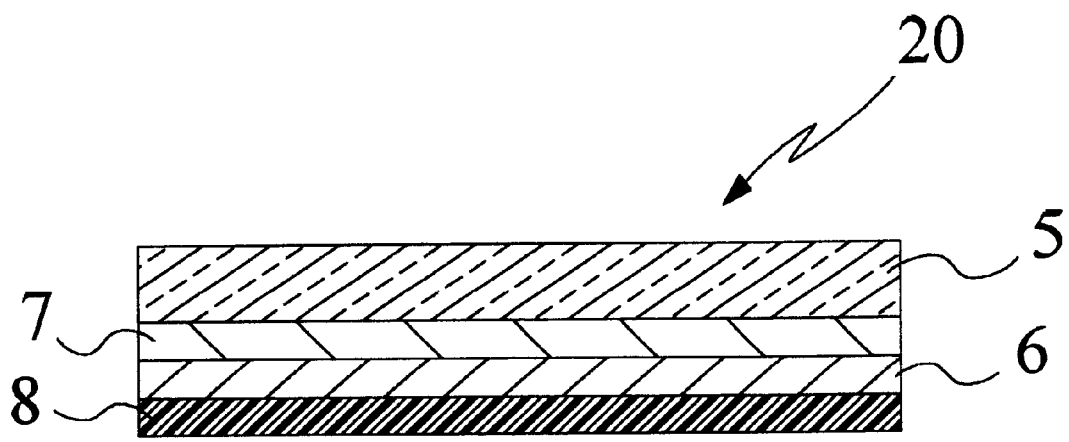
FIG. 2 is a cross-section of a preferred embodiment of the sensor film layer system.

In FIG. 2, chemochromic film 20 uses a layer system comprising a layer of tungsten trioxide ($WO_3$) 6, deposited by vacuum thermal evaporation onto glass substrate 5, to a thickness of approximately 500 nm. A very thin layer of palladium 6, approximately 2.2 nm thick, is also deposited by vacuum thermal evaporation on top of the tungsten trioxide layer. The layer system can further comprise, as in the preferred embodiment, a polymer layer of TEFLON 8, to a thickness of approximately 100–1000 nm, to inhibit water and other contaminants from reaching the film layer 20, 6, and 7. While it is preferred that the deposition of film layer 20, 6, and 7, onto substrate 5, is by vacuum thermal evaporation, it may be accomplished by any other method, well know in the art, including, without limitation, rf-, and dc-sputtering, and laser ablation. Chemochromic film 20 is transparent when not in the presence of hydrogen. When hydrogen gas reversibly reacts with the tungsten trioxide, the film changes to a blue color ($H_xWO_3$) which grows in intensity as the concentration of hydrogen (x in the formula, $H_xWO_3$) increases. When hydrogen gas is displaced from the vicinity of film 20, the hydrogen in the $H_xWO_3$ diffuses to the surface of film 20 and escapes either as hydrogen gas, or is oxidized to water, if oxygen is present.

When hydrogen is produced, in small quantities, near the sensor coating, as for example with colonies of green algae, the local coloration of the film, as outlined within the grid, identifies the location of the hydrogen-producing colony. In this way, the film helps to identify which, among many plated colonies of algae are producing hydrogen gas under experimental conditions.

EXAMPLE

Wild type *C. reinhardtii* (WT) was obtained from the University of Colorado at Boulder and a cell-wall-less strain of *C. reinhardtii* (cw15) was obtained from the Chlamydomonas Genetics Center, Duke University. Algal cell suspensions were grown photoautotrophically either in Sager's minimal medium (WT), or in a modified Sueoka'a high salt medium, as described in Ghirardi et. al., Development of an Efficient Algal $H_2$-Producing System, *Proceedings of the 1996 U.S. DOE Hydrogen Program Review*, Vol. I, 285–302, (1997). Suspension cultures were grown under illumination at 25° C., using cool white fluorescent lights (8 W/m$^2$), and agitated with a bubble mixture of 1.7% $CO_2$ in air. Plated colonies were prepared by centrifugation of suspension cultures. Harvesting of cell suspensions was done at 2000 g, for 10 minutes, and resuspended cells were inoculated on either 1.5% (WT), or 0.8% (cw15) agar gel in sterile plastic Petri dishes.

Mutageneses

In order to generate *C. reinhardtii* mutants to be used in the two selective pressure methods described above, the cultures were exposed to nitrosoguanidine ("NTG"), a chemical mutagen that induces random point mutations in algae, according to the method of Harris E., *The Chlamydomonas Sourcebook*, Academic Press, New York (1989). The random point mutations were induced in an algal cell suspension (3×10$^6$/ml), in citrate buffer (0.025 M sodium citrate, pH 5.0), with 1 μg/ml NTG for 30 minutes, in the dark. We had previously determined that this induction protocol kills 50% of the cell-wall-less cells in suspension. The cell suspensions were then washed to remove any residual NTG, suspended in growth medium, and incubated for two to three days, under illumination, in order to allow for chromosome segregation and mutational expression. Finally, a dark aerobic starvation of the cells followed, for two to three days, to deplete the internal cellular storage reserve prior to hydrogen-uptake selective pressure.

Hydrogen-Uptake Selective Pressure

Selection using hydrogen-uptake conditions was first applied by McBride et al, Mutational Analysis of *Chlamydomonas reinhardtii*, Application to Biological Solar Energy Conversion, *Biological Solar Energy Conversion*, 77–86, Academic Press, New York, N.Y. (1977), who subjected a population of WT cells to photoreductive conditions in the presence of controlled oxygen concentrations. Surviving algal cells grew by fixing carbon dioxide with electrons obtained from the oxidation of hydrogen (using hydrogenase hydrogen-uptake activity) and adenosine triphosphate generated by a cyclic electron transfer around photosystem I. Photosynthetic water oxidation was blocked by the presence of a photosystem II inhibitor, dicholoromethlyurea ("DCMU"). This selective pressure has been much more specific for oxygen-tolerant organisms than for hydrogen production selection.

Based on the McBride, et al. disclosure, we used an optimized hydrogen uptake selective pressure procedure on the above mutagenized suspension. The hydrogen-uptake selective pressure was applied by treating a liquid culture of the mutagenized wild-type *C. reinhardtii* cells with a 10–100 μM DCMU, or 15 μM DCMU and 15 μM atrazine, solution, to eliminate photosynthetic oxygen evolution. The cultures were then incubated under low light conditions, in anaerobic jars, containing a nitrogen gas mixture, having approximately 10% hydrogen, 1% carbon dioxide, and 8–10% oxygen, for seven days in order to eliminate the wild-type and undesirable phenotypes. After seven days, the surviving oxygen-tolerant mutant cells were washed in growth medium, and plated on sterile minimal agar. Surviving colonies were counted after growing under illumination conditions for three weeks.

The addition of oxygen, to the selective pressure, decreased the number of survivors by 3–4 orders of magnitude because of the inactivation of oxygen-sensitive hydrogenase. When the cells were cultured in oxygen for more than seven days, the cell density increased once again due to replication of the oxygen-tolerant survivors.

Screening

An individual 3 mm diameter colony of green algae growing on agar contains about 1 μg of chlorophyll. We had previously determined that this colony can photo-evolve hydrogen, under anaerobic conditions, at a maximum measurable rate of about 80 μmoles of hydrogen per milligram of chlorophyll per hour. Thus, the theoretical yield of this colony is 4 nmoles of hydrogen in the two minutes prior to deactivation of the hydrogenase enzyme, by oxygen, as a result of photosynthesis. We have considered this number to be the minimum desired sensitivity for screening organisms suspected of having the oxygen-tolerant hydrogen phenotype.

Figure 3:
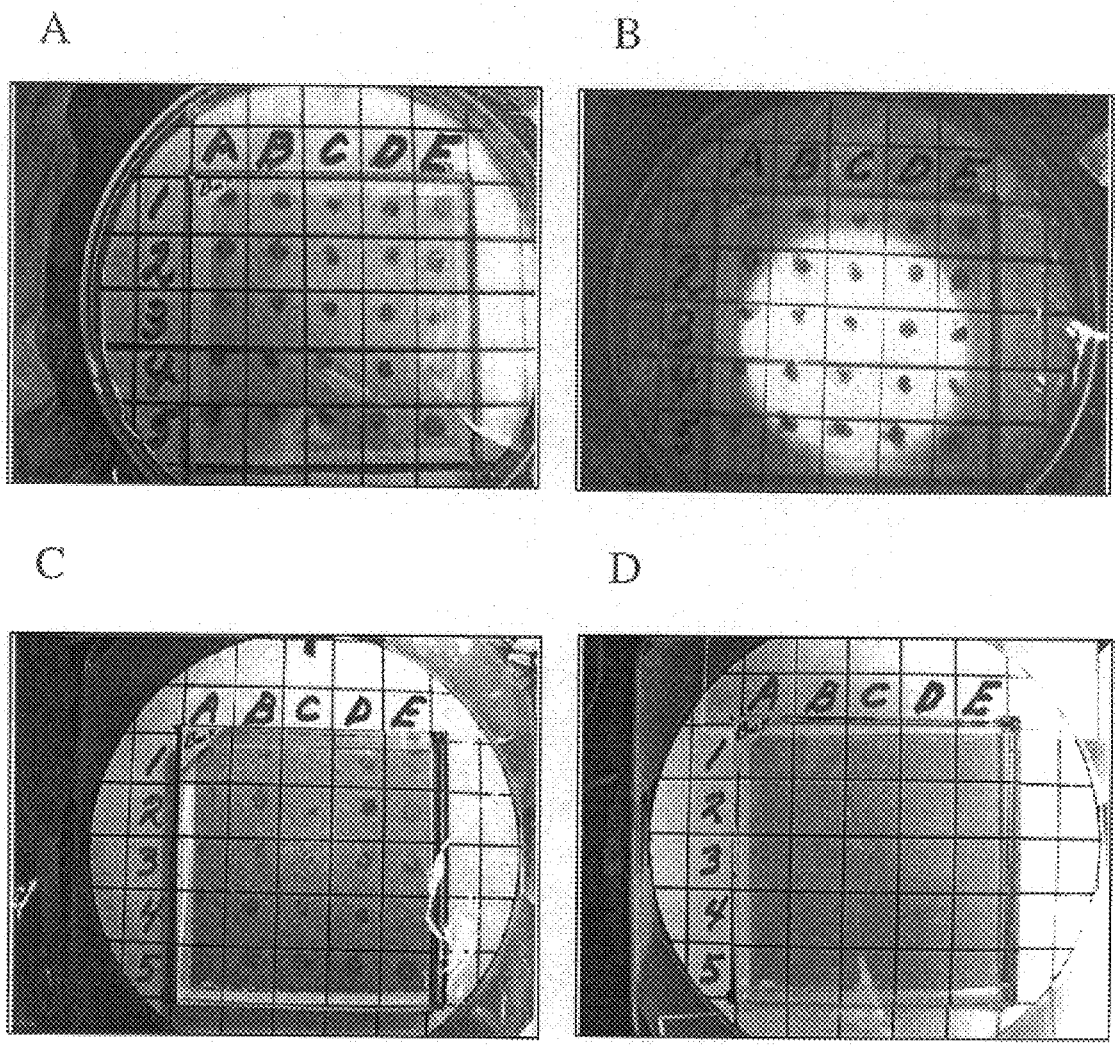
FIG. 3A is a top view of an agar plate having surviving green algae mutant colonies obtained through selective pressure.
FIG. 3B shows the sensitization reaction. The chemochromic film is positioned over the filter paper, and the algae are illuminated with saturating light to induce hydrogen production.
FIG. 3C shows a color change in the chemochromic film (note the round spots), which spatially identifies the isolated colonies that produce hydrogen. The chemochromic film has been removed from the agar place and has been placed on a white background.
FIG. 3D, shows the reversible nature of the color reaction after exposure of the film to air for 5 minutes, following the sensitization reaction, and hence the confirmation that hydrogen was in fact detected.

A sterile piece of filter paper was positioned on top of the plated mutant colonies surviving hydrogen-uptake selection pressure, and the hydrogenase was induced by subjecting the colonies to an anaerobic atmosphere for 4 hours. The sensor film, of the invention herein, was placed on top of the filter paper and the plates were illuminated by a light source 30, as seen in FIG. 1, to generate hydrogen production, in the sensitization reaction. Hydrogen-induced, chemochromic sensor color change results were recorded as illustrated in the following figures. FIG. 3A shows one agar plate containing several different surviving algal isolate colonies. The colonies are covered with a piece of filter paper 15 and the locating grid 35, see also, FIG. 1. FIG. 3B shows placement of the chemochromic film over the filter paper, and colonies of algae. In FIG. 3B, the colonies shown are illuminated from the bottom of the agar plate with saturating light causing the induction of hydrogen production, in the sensitization reaction. In FIG. 3C, the chemochromic sensor film has been removed from the plastic dish and each dark spot, on the film, corresponds to the grid location covering the hydrogen-producing algal colony causing the color change. Finally, in FIG. 3D, the reversible nature of the color change is demonstrated. Here, the color change spots have disappeared after exposure of the film for 5 minutes in air, following the sensitization reaction. This disappearance is confirmation of the fact that hydrogen has evolved for each surviving colony having the oxygen-tolerant hydrogen phenotype.

These results demonstrate that the chemochromic sensor film is sensitive enough to detect nanomoles of hydrogen produced by individual colonies of algae and that this sensor is, therefore, useful to rapidly screen a large number of colonies for hydrogen production capacity. Preliminary experiments have also confirmed a measured quantitative relationship between the intensity of the sensor film color change and the amount of hydrogen produced.

Colonies that had exhibited a light blue color change, and a dark blue color change were raised separately, in liquid culture. The hydrogenase enzyme was then induced, in each culture, and the initial rates of hydrogen evolution were measured by amperometric measurement. The culture which had exhibited the dark blue sensor film color change had a higher initial rate of hydrogen production compared to cultures which exhibited the light blue color change. Thus far, after one round of selection and screening, according to the invention herein, the best mutant produced hydrogen at a rate of four times that of the WT organism, and was about three times less sensitive to oxygen.

We claim:

1. A method for identifying a hydrogen-gas-producing organism comprising the steps of:

(a) isolating the organism on a substrate;

(b) providing a sensor film having a first layer comprising a transition metal oxide or oxysalt and a second layer comprising a hydrogen-dissociative catalyst metal, the first and second layers having an inner and an outer surface wherein the inner surface of the second layer is deposited on the outer surface of the first layer;

(c) positioning the outer surface of the second layer proximal to the substrate; and (d) identifying the organism by inducing the evolution of hydrogen gas, the gas causing a change in the color of the film.

2. The method of claim 1, wherein the transition metal oxide is selected from the group consisting of $WO_3$, $Nb_2O_3$ and $CoMoO_4$.

3. The method of claim 1, wherein the hydrogen dissociative catalyst metal is selected from the group consisting of rhodium, platinum, and palladium.

4. The method of claim 1, further comprising providing a fluorinated hydrocarbon polymer between the outer surface of the second layer and the substrate, the fluorinated hydrocarbon applied to the outer layer of the hydrogen dissociative catalyst metal.

5. The method of claim 4 wherein the fluorinated hydrocarbon polymer comprises polytetrafluoroethylene.

6. The method of claim 1, further comprising a means for separating the substrate from the outer surface of the second layer.

7. The method of claim 6, wherein the separating means comprises filter paper.

8. The method of claim 1, further comprising providing a means for associating a location of the hydrogen producing organism on the substrate in relation to the color change on the film.

9. The method of claim 8, wherein the associating means comprises a grid system comprised of a matrix of cells positioned in a spaced relationship to the substrate, a single colony of the microbe circumscribed by reference to a cell of the grid.

10. The method of claim 1, wherein the color change comprises a variable intensity on the film.

11. The method of claim 10, wherein the variable intensity is a function of the hydrogen gas concentration evolved by the microorganism to be identified.

* * * * *